(12) United States Patent
Mahoney

(10) Patent No.: US 10,842,699 B2
(45) Date of Patent: Nov. 24, 2020

(54) SYSTEM AND METHOD FOR PATIENT POSITIONING IN AN AUTOMATED SURGERY

(71) Applicant: Ormonde M. Mahoney, Athens, GA (US)

(72) Inventor: Ormonde M. Mahoney, Athens, GA (US)

(*) Notice: Subject to any disclaimer, the term of this patent is extended or adjusted under 35 U.S.C. 154(b) by 435 days.

(21) Appl. No.: 15/965,376

(22) Filed: Apr. 27, 2018

(65) Prior Publication Data

US 2019/0328599 A1 Oct. 31, 2019

(51) Int. Cl.
| | |
|---|---|
| *A61G 13/12* | (2006.01) |
| *A61B 34/00* | (2016.01) |
| *A61B 34/20* | (2016.01) |
| *A61B 34/30* | (2016.01) |
| *A61G 13/00* | (2006.01) |
| *A61G 13/10* | (2006.01) |
| *A61B 90/50* | (2016.01) |

(52) U.S. Cl.
CPC .......... *A61G 13/1245* (2013.01); *A61B 34/20* (2016.02); *A61B 34/30* (2016.02); *A61B 34/70* (2016.02); *A61B 90/50* (2016.02); *A61G 13/0063* (2016.11); *A61G 13/101* (2013.01)

(58) Field of Classification Search
CPC ............ A61G 13/1245; A61G 13/0063; A61G 13/101; A61G 13/1295; A61B 34/70; A61B 34/20; A61B 34/30
See application file for complete search history.

(56) References Cited

U.S. PATENT DOCUMENTS

| | | | | |
|---|---|---|---|---|
| 3,990,122 | A | * 11/1976 | Peterson | A47C 19/022 5/651 |
| 4,240,170 | A | * 12/1980 | Thumberger | A47C 20/022 5/651 |
| 5,645,079 | A | 7/1997 | Zahiri et al. | |
| 5,740,571 | A | * 4/1998 | Tyra | A47C 20/022 5/624 |
| 7,725,162 | B2 | 5/2010 | Malackowski et al. | |
| 9,119,655 | B2 | 9/2015 | Bowling et al. | |
| 2004/0133984 | A1 | * 7/2004 | Mahoney | A61G 13/0081 5/651 |
| 2013/0211792 | A1 | * 8/2013 | Kang | G09B 23/30 703/1 |
| 2015/0250672 | A1 | 9/2015 | Fossez et al. | |

* cited by examiner

*Primary Examiner* — Eric J Kurilla
(74) *Attorney, Agent, or Firm* — Smith Tempel Blaha, LLC; Matthew T. Hoots

(57) ABSTRACT

The present solution is generally directed to a patient positioning system used to position body parts, such as a knee, during a medical or surgical procedure. Further, the present solution is generally directed to a system and method for establishing and tracking virtual boundaries, and controlling a patient positioning system to adjust those virtual boundaries to facilitate an automated surgery procedure. Further, the present solution is generally directed to the synergistic combination of an autonomous patient positioning sub-system with a robotic surgical manipulator sub-system.

14 Claims, 7 Drawing Sheets

SYSTEM AND METHOD FOR PATIENT POSITIONING IN AN AUTOMATED SURGERY

TECHNICAL FIELD

The present solution is generally directed to a patient positioning system used to position body parts, such as a knee, during a medical or surgical procedure. The present solution also is generally directed to a system and method for controlling a surgical manipulator and a patient positioning system based on automated surgical parameters. Further, the present solution is generally directed to a system and method for establishing and tracking virtual boundaries, and controlling a patient positioning system to adjust those virtual boundaries to facilitate an automated surgery procedure.

Further, the present solution is generally directed to the synergistic combination of an autonomous patient positioning sub-system with a robotic surgical manipulator sub-system. The combination of the autonomous patient positioning sub-system with the robotic surgical manipulator sub-system is ready, relatively simple to accomplish, and relatively easy to program in conjunction with the pre-existing software and hardware for the autonomous or partially-autonomous combination system.

PRIOR ART

Orthopedic surgeons have found it useful to use robotic devices to assist in performing surgical procedures. Generally, these robotic devices comprise a moveable arm with one or more linkages, and a free distal end, with an attached surgical instrument, that can be accurately and precisely applied to the surgical site. The practitioner, with the aid of computer software, machine learning, and/or specialty algorithms for sensory input, is able to position the arm so as to position the surgical instrument at the site on the patient at which the instrument is to perform the surgery.

Advantageously, the robotic device, unlike the surgeon, is not subjected to muscle strain, fatigue, or involuntary movements. Thus, in comparison to when an instrument is hand-held and, therefore, hand positioned and supported, it is possible to use the robotic device to hold an instrument steady and consistently, and move the instrument along a defined path with a high degree of accuracy and precision.

Further, some robotic devices are designed to be used with surgical navigation systems. Generally, a navigation system is configured to process sensor data and provide an indication of the location of the surgical instrument relative to the location of the patient against which the instrument is applied. In some instances, virtual boundaries are created using computer aided design software to delineate areas in which an end surgical tool of a robotic device/system can maneuver from areas in which the end surgical tool cannot. This substantially eliminates the likelihood that the instrument will act, or be requested to act, outside its intended bounds/margins (i.e., too much being done, or treatment being performed on the incorrect location). Conversely, this substantially eliminates the likelihood that the instrument will not act, or be requested to not act, on the intended bounds/margins (i.e., too little being done).

More specifically, when a robotic device is provided with data indicating the relative location of the instrument, the robotic device may be configured to autonomously or semi-autonomously position the instrument to ensure that it is applied to the intended site on the patient. In orthopedic surgery, a virtual cutting boundary is created to delineate sections of bone to be removed by the end surgical tool during the surgery from sections of bone that are to remain after the surgery. The navigation system tracks movement of the end surgical tool with respect to the virtual cutting boundary to determine a position and/or orientation of the end surgical tool relative to the virtual cutting boundary. The robotic system cooperates with the navigation system to guide movement of the end surgical tool so that the end surgical tool does not move beyond the virtual cutting boundary.

Typically, virtual cutting boundaries are created prior to surgery. Virtual cutting boundaries are created in a model of a patient's bone, and fixed with respect to the bone, so that when the model is loaded into the navigation system, the navigation system tracks movement of the virtual cutting boundary by tracking movement of the bone. Virtual boundaries also define other anatomical features to be avoided by the end surgical tool during surgery. Such features include nerves or other types of tissue to be protected from contact with the end surgical tool. Virtual boundaries also are used to provide virtual pathways that direct the end surgical tool toward the anatomy being treated. These examples of virtual boundaries may be fixed in relationship to the anatomy being treated, or the boundaries may be dynamic and tracking of the anatomical features, and other objects in the operating room or surgical space, which may move relative to the anatomy being treated.

During performance of an orthopedic surgical procedure, a number of different surgical components are typically positioned at the surgical site. Further, there is a need to properly position a patient, including a limb, for the procedure. Some procedures require that the patient or patient's limb be re-positioned during different parts of the procedure. One method of positioning patients during surgical procedures has been the use of an assistant surgeon or other trained personnel to on-site, manually operate, maneuver, and judge the position adjustments of the patient. The trained personnel performs, at least in part, via specialty patient positioning tools/devices. However, this method has several disadvantages including the costs involved with using additional operating-room personnel (to operate the patient positioning tools/devices), and the risk involved with positioning that personnel proximate to the sterile operating field (which risks infection).

Therefore, there is a need in the art to provide a system and method for controlling automated patient positioning devices in conjunction with established or establishing virtual constraint boundaries.

Providing some further context, certain exemplary embodiments of the present solution are directly applicable to arthroplasty. In the case of both knee and hip arthroplasty, this procedure can help relieve pain and restore function in a severely diseased joint. This treatment option involves cutting away damaged bone and cartilage (with an end surgical tool, for example) and replacing it with an artificial joint made of metal alloys, high-grade plastics and/or polymers. This type of treatment procedure known in the art produces reliable symptomatic relief and improved function.

Prior to placing the patient on a surgical table, it is common practice to place a sterile drape on the table. This drape functions as a sterile barrier. Some available limb holders for arthroplasty are designed to be attached directly to the tables with which the holders are used. At the location where this type of limb holder is attached it is difficult, if not impossible to, place the drape around and/or under the limb holder so as to provide the desired sterile barrier.

More specifically, hip and knee joint replacements are the most commonly performed joint replacement surgical procedures in which parts of an arthritic or damaged joint is removed and replaced with a metal, plastic or ceramic device termed joint implants. Joint implants or what commonly can be referred to as prosthetic joints, are long-term implantable surgical devices that are used to either completely or partially replace the structural elements within the musculoskeletal system to improve and enhance the function of a joint.

Physiology changes to the above mentioned joint structures are thought to contribute towards the progression of a diseased knee joint leading to the consideration of joint replacement surgery. Some of these changes include: measureable differences in overall knee cartilage volume and tibial cartilage volume, measurable differences in bone size, meniscal tears and bone marrow lesions.

Pursuant to the foregoing, it may be regarded as an object of the present solution to overcome the deficiencies of, and provide for improvements in, the state of the prior art as described above, and as may be inherent in the same, or as may be known to those skilled in the art. It is a further object of the present solution to provide a surgical device and method of use thereof, for carrying out the same, and of the foregoing character, and in accordance with the above objects, which may be readily carried out, with and within the process, and with comparatively simple equipment, and with relatively simple engineering requirements. Still further objects may be recognized and become apparent upon consideration of the following specification, taken as a whole, wherein by way of illustration and example, an embodiment of the present solution is disclosed.

As used herein, any reference to an object of the present solution should be understood to refer to aspects and advantages of the present solution, which flow from its conception and reduction to practice, and not to any a priori or prior art conception.

The above and other objects of the present solution are realized and some limitations of the prior art are overcome in the present solution by providing new and improved methods, processes, compositions, and systems. A better understanding of the principles and details of the present solution will be evident from the following description.

BRIEF SUMMARY OF THE SOLUTION

An exemplary embodiment of the present solution relates to a system and method for positioning a patient in an automated surgical environment.

An exemplary embodiment of the present solution also relates to an autonomous patient positioning system and method of operation (1) that is simple in construction, (2) that is easy to integrate with an orthopedic robotic surgery device/system, (3) that is positioned outside the sterile operating field, and (4) that allows for manual positioning of the patient, in and out of the patient positioning system, when necessary, without the patient having to be physically strapped (at the upper leg or foot, for example), and (5) yet permits a system processor(s), as monitored and supervised by a surgeon, to readily position, adjust, and/or re-position a patient's limbs during the automated surgical procedure.

In accordance with one aspect of the present solution, an autonomous patient positioning device is provided and includes a support adapted to be positioned against a predetermined portion of a patient's body; a drive mechanism for moving the support along a generally linear path; a source of power for the drive mechanism; a bracket for mounting the drive mechanism to an operating table; and a remote device for actuating the drive mechanism. The remote device uses, at least in part, a plurality of dynamic virtual boundaries to guide movement of the patient positioning device/sub-system.

In a preferred form, the support is padded to provide additional comfort for a patient. In one embodiment, the support is generally cylindrical in shape. The support may be adapted to be positioned against any predetermined portion of a patient's body. In one embodiment of the solution, the support is designed to be positioned against the foot of a patient.

Further, the drive mechanism may comprise a number of electrically, hydraulically, or pneumatically operated devices. In one embodiment of the solution, the drive mechanism comprises an electrically powered linear actuator. In a preferred form, the support includes an extension, preferably angled, and the drive mechanism is coupled to the extension. Preferably, the extension includes means for adjusting the height of the support. In one embodiment of the solution, the means include a plurality of generally spaced openings on the extension and a pin for releasably locking the extension in a predetermined position through such spaced openings.

The device of the present solution provides convenience for the surgeon by permitting remote and autonomous "smart" operation of the drive mechanism. The present solution also provides a method for positioning a patient during a surgical procedure comprising positioning a patient on an operating table; positioning a movable support against a predetermined portion of a patient's body outside of the sterile operating field; causing the support to move by actuating a drive mechanism to provide linear movement of the support to cause the patient to move to an optimal position for a surgical procedure.

In certain exemplary embodiments, the autonomous patient positioning sub-system is communicatively coupled with a navigation system, and indirectly to a surgical manipulator for applying an instrument or surgical tool to a patient. The navigation system is configured to cooperate with the autonomous patient positioning sub-system to position the support. The navigation system includes a navigation processor and a boundary generator module operable on the navigation processor or any other processor. The boundary generator module is configured to generate the boundary based on a plurality of inputs including data defining an implant to be fitted to the patient, for example, and data defining how relative changes to the patient positioning sub-system affect the position and pose of the tissue of the patient receiving the implant.

In certain exemplary embodiments, the system comprises a support portion tracking device to track movement of the support. The system may also comprise a first boundary tracking device to track movement of a first of the plurality of virtual boundaries wherein the first virtual boundary is associated with the anatomy to be treated. The system may further comprise a second boundary tracking device to track movements of a second of the plurality of virtual boundaries wherein the second virtual boundary is associated with an object to be avoided by the surgical tool or instrument. A controller is configured to receive information associated with the tracking devices including positions of the system portion relative to the first and second virtual boundaries. The controller is configured to guide movement of the support portion of the patient positioning sub-system relative to each of the first and second virtual boundaries as the first and second virtual boundaries move relative to one another.

In a preferred embodiment, the movable support is positioned against the patient's heel and foot. Movement of the support causes flexing of the patient's knee to a target position for a surgical procedure. Depending on the surgical procedure to be performed, the support may be moved to a second position during the surgical procedure, etc. Additional movement of the support during surgery is possible and simplified, depending upon the need for re-positioning of the patient.

A method of controlling the support of the patient positioning sub-system is also provided. The method includes providing the patient positioning sub-system to properly position a patient at certain points during a surgical procedure. The navigation system cooperates with the patient positioning sub-system to position the support with respect to a boundary between tissue of the patient to which the surgical tool should be applied and tissue of the patient to which the tool should not be applied. The boundary is generated based on a plurality of inputs.

In another embodiment, a method is provided for using a plurality of dynamic virtual boundaries to guide movement of the support of the patient positioning sub-system. The method includes tracking movement of the support and a first virtual boundary associated with the anatomy to be treated. The method further includes tracking movement of a second virtual boundary relative to the first virtual boundary wherein the second virtual boundary is associated with an object to be avoided by the surgical instrument. Movement of the support is guided relative to each of the first and second virtual boundaries as the first and second virtual boundaries move relative to one another.

One advantage of these embodiments is the ability to dynamically track objects (such as other tools or anatomy) that may move relative to the anatomy of interest, in addition to tracking the patient positioning sub-system. The second virtual boundary can be a virtual constraint boundary or other type of virtual boundary that is tracked for movement relative to the first virtual boundary associated with the anatomy.

Embodiments of the system and sub-systems described herein, according to the solution, are not limited to the exemplary aspects and features described above or below. Certain embodiments may include additional features, or different features, while other embodiments include alternative features.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

DETAILED DESCRIPTION OF PREFERRED EMBODIMENTS

Figure 1:
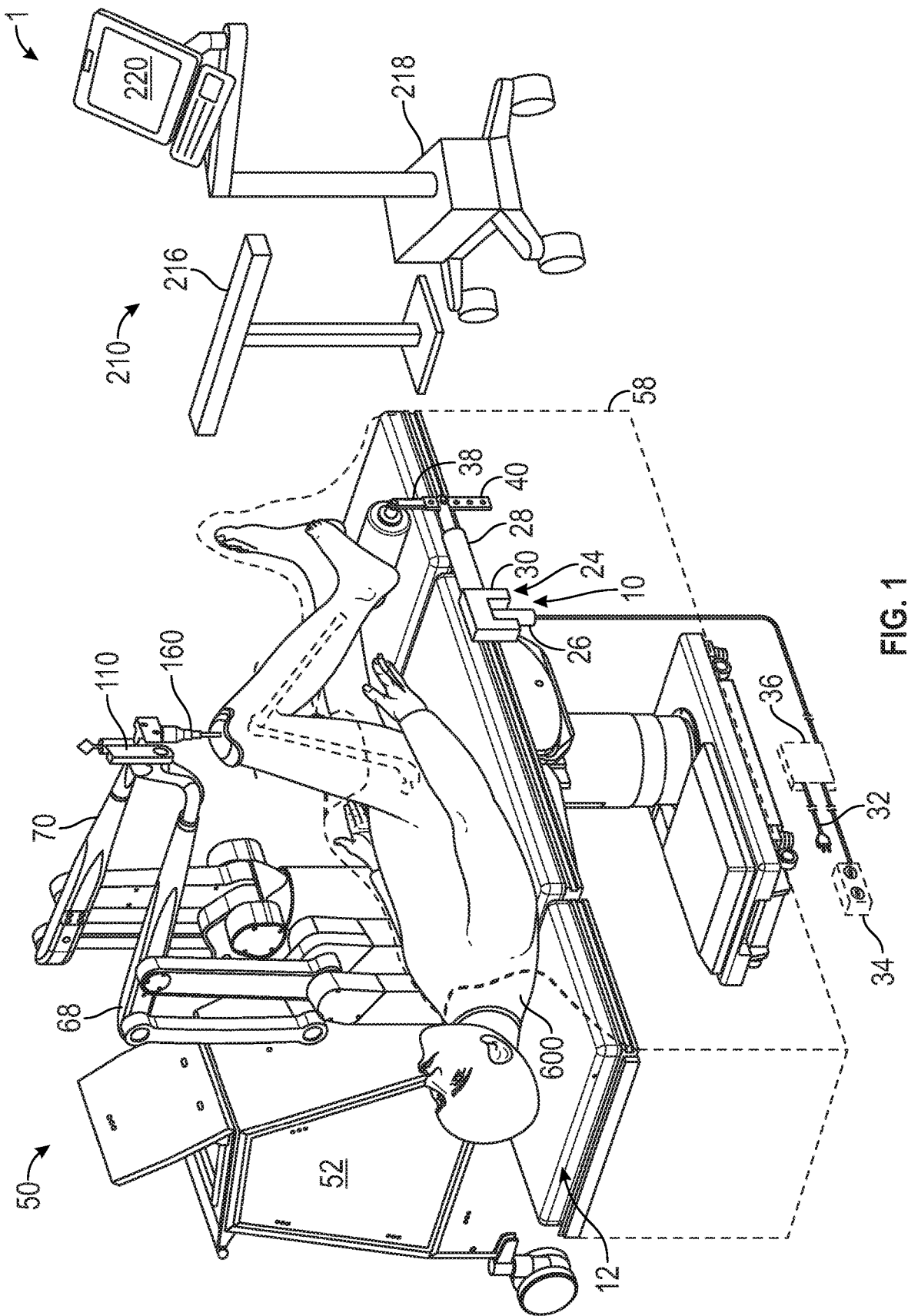
FIG. 1 is an illustration of an exemplary embodiment of a new and useful system that positions a patient, via an autonomous patient positioning sub-system, and which operates in conjunction with a robotic surgical manipulator device.

For a further understanding of the nature, function, and objects of the present solution, reference should now be made to the following detailed description. While detailed descriptions of the preferred embodiments are provided herein, as well as the best mode of carrying out and employing the present solution, it is to be understood that the present solution may be embodied in various forms. Therefore, specific details disclosed herein are not to be interpreted as limiting, but rather as a basis for the claims and as a representative basis for teaching one skilled in the art to employ the present solution in virtually any appropriately detailed system, structure, or manner.

The word "exemplary" is used herein to mean serving as an example, instance, or illustration. Any aspect described herein as "exemplary" is not necessarily to be construed as exclusive, preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component.

One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

In this description, the terms "central processing unit ("CPU")," "digital signal processor ("DSP")," "graphical processing unit ("GPU")," "processing component" and "chip" are used interchangeably. Moreover, a CPU, DSP, GPU or chip may be comprised of one or more distinct processing components generally referred to as "core(s)."

The present solution is based, at least in part, on a new and useful patient positioning system that autonomously positions a patient for a number of surgical procedures including, but not limited to, total hip replacement, lumbar surgery, open reduction internal fixation of the elbow, open reduction internal fixation of the femur, foot fusion, posterior cruciate ligament reconstruction, shoulder repairs, total shoulder replacement, spinal fusion, open reduction internal fixation of the tibia, anterior cervical discectomy and fusion of the neck, arthroscopic anterior cruciate ligament reconstruction, arthroscopic knee evaluation, and partial and total knee replacement. It will also be understood that the construction of the support portion of the system/sub-system may be modified to accommodate specific body parts depending upon the surgical procedure being performed. While certain exemplary embodiments in the following detailed description are made with respect to positioning a patient's knee for a surgical procedure, it will be understood that the solution encompasses other surgical procedures and that the following description is made with reference to a preferred embodiment thereof and to simplify understanding of the solution.

At a very high level, an exemplary embodiment of the present solution relates to an apparatus for positioning a patient on an operating table—or a patient positioning sub-system.

An exemplary embodiment of the patient positioning sub-system of the present solution includes a support that is adapted to be positioned against a predetermined portion of a patient's body, such as beneath the patient's foot, for example. The patient positioning sub-system also includes a drive mechanism for moving the support along a generally linear path. The drive mechanism may be electrically, hydraulically, or pneumatically powered. In a preferred embodiment, the drive mechanism comprises an electrically powered linear actuator.

Further, a bracket is used to secure the drive mechanism to a support rail of a surgical operating table or bed. Thumbscrews, clamps, or other attachment devices are used. The bracket and attachments are designed so that the drive mechanism is readily moveable from one side of an operating table to an opposite side or end, depending upon the particular surgical procedure to be performed.

Further, the support may be padded for patient comfort. In a preferred embodiment, the support is in the form of a cylinder; however, it is envisioned that the support may take different forms as required by the surgical procedure selected.

In use, in an exemplary embodiment, a patient is positioned on the operating table and the patient positioning sub-system is installed so that the movable support is properly positioned against a predetermined portion of the patient's body (the support is positioned beneath the foot of the patient, for example). The patient positioning sub-system and/or the movable support may then be positioned and used outside of the sterile operating field (below the sterile drape, for example), advantageously not interfering with a patient's, surgeon's, and/or other surgical assistant's movement.

As is presented in detail herein, in some surgical procedures, it is necessary to move a patient's limb or body to a first position for initial work and then to move that limb or body portion to second, third or more optimal positions as the surgery proceeds. The patient positioning system of the present solution facilitates this end better than any system known or used in the art.

The present solution also is based, at least in part, on a new and useful system that positions a patient, via an autonomous patient positioning sub-system, in conjunction with a robotic surgical manipulator device that positions a surgical instrument or tool for use on the patient, wherein the positioning of the patient is based at least in part on the demands and requirements and boundary-requirements, etc. of the robotic surgical manipulator device.

Robotic surgical manipulator device(s) usually comprise a moveable arm with one or more linkages, and a free distal end, with an attached surgical instrument or tool, that can be accurately and precisely applied to the patient, and the necessary computing, processing, and transmission hardware to make the system work. When robotic device(s) are provided with data indicating the relative location of the instrument, the robotic device(s) are configured to autonomously or semi-autonomously position the instrument to ensure that it is applied to the intended site on the patient.

Virtual cutting boundaries are created to delineate sections available to the instrument and section restricted to the instrument. Navigation system(s), for example, track movement of the end surgical tool with respect to the virtual cutting boundary to determine a position and/or orientation of the end surgical tool relative to the virtual cutting boundary. Navigation system(s) also interface with other known computer hardware component(s) to actuate the end surgical tool. The present disclosure explores the benefits of incorporating an automated patient positioning system.

As such, an exemplary embodiment of the patient positioning sub-system of the present solution, configured to operate in conjunction with a robotic surgical manipulator device, comprises a surgical processing component/sub-system configured to process data from the system, to provide an indication of the location of the surgical instrument relative to the location of the patient, and to assess the state, position, and/or condition of the components or sub-components and how that information relates to the virtual boundaries. For example, the surgical processing component/sub-system may be configured to receive and process sensor data and/or component data to create virtual boundaries for the surgery, and to process the position of the movable portions of the patient positioning sub-system, and to assess how relative changes to the position of the movable portions affect accessibility to the patient tissue and/or locations defined by the virtual boundaries.

The exemplary embodiment of the patient positioning sub-system also comprises a controller sub-system, to which the surgical navigation sub-system communicates information, for which the controller sub-system uses to appropriately actuate the patient positioning sub-system (actuating back and forth movement of the support of the patient positioning sub-system, relative to the surgical table's longitudinal axis, for example—towards the feet of the table or towards the head of the table).

As is presented in detail herein, during performance of an orthopedic surgical procedure, a number of different surgical components are typically positioned at the surgical site. For example, joint components such as trial implants are positioned at the surgical site to determine the appropriately sized implant components that should be permanently fitted to the patient. Other examples include retractors and trackers, etc. as well as any other surgical instrument known to a person having ordinary skill in the art Further, some anatomical features, or other objects in the operating room, may move relative to the anatomy being treated. For instance, retractors used to provide an opening in tissue for a surgical tool, an instrument, etc. may move relative to the anatomy being treated. If not accurately tracked using an appropriate dynamic virtual constraint boundary system, for example, the robotic surgical manipulator devices may inadvertently strike objects or boundaries that are not desired and/or provide incorrect information to the person overseeing the surgery. If overly restricted, a surgeon using the robotic surgical manipulator devices is not afforded the full capability necessary to finish complex and dynamic surgeries.

Further, and as context, in current practice, each joint component of an orthopedic joint system is typically packaged separately. Due to manufacturing variation, each of these joint components has dimensions which vary slightly from others of their type. A typical knee replacement will use three or more joint components. The collective variation of these dimensions is known as dimensional stack-up.

In conventional knee replacement surgery, the dimensional stack-up is relatively small compared to other potential sources of alignment and placement error such as jig placement or cut errors. Options are available for users to change joint components in order to make up for these collective errors and achieve a proper and optimal fit.

There is therefore a need to improve prior art patient positioning sub-systems and prior art robotic surgical manipulator devices to resolve these issues, and various other issues. The exemplary embodiments of the patient positioning sub-system, in conjunction with a robotic surgical manipulator device, of the present solution, facilitates this end better than any system known or used in the art.

The present solution also is based, at least in part, on a new and useful system that positions a patient, via a patient positioning sub-system, operated in conjunction with a robotic surgical manipulator device, wherein the positioning of the patient is an autonomous mode, coordinated with the application of the surgical instrument or tool of the surgical manipulator. More specifically, the surgical instrument of the robotic surgical manipulator device determines the relative location of the instrument to a boundary, and determines the relative location/positioning of the patient positioning sub-system (the support of the patient positioning sub-system, for example), with the patient in place. This boundary defines the limits of the tissue beyond which the instrument should not be placed. In the event it appears that the robotic surgical manipulator device demands, requires, or needs positioning of the instrument beyond the boundary, the manipulator does not allow this movement of the instrument.

For example, should the robotic surgical manipulator device determine that the needed path/point for the instrument would result in the instrument exceeding a boundary, which the instrument should not cross, the surgical manipulator (1) prevents the instrument from movement beyond the boundary, and (2) adjusts the patient positioning sub-system (the support of the patient positioning sub-system, for example, and/or any other component or sub-system of the patient positioning sub-system) to reposition the tissue to be treated, and (3) reassesses/determines the relative location of the instrument to the new boundary condition, after adjustment of the patient positioning sub-system at (2). The robotic surgical manipulator device may then continue to attempt to move the instrument as demanded, required, or needed prior to (1).

In this way, at a very high level, an exemplary embodiment of the present solution relates to a robotic surgical device that realizes the synergistic combination of an autonomous patient positioning sub-system with a robotic surgical manipulator sub-system, the combination for positioning a surgical instrument for use on the patient, and for controlling the surgical instrument based on tissue parameters and/or implant parameters and/or the parameters of the patient positioning sub-system (the support of the patient positioning sub-system, for example).

Described in an alternative way, an exemplary embodiment of the present solution relates to a robotic surgical device that realizes the synergistic combination of an autonomous patient positioning sub-system with a robotic surgical manipulator sub-system. The combination of the autonomous patient positioning sub-system with the robotic surgical manipulator sub-system is ready, relatively simple to accomplish, and relatively easy to program in conjunction with the programming for the autonomous or partially-autonomous robotic surgical manipulator sub-system as described herein. Advantageously, the combination of the autonomous patient positioning sub-system with the robotic surgical manipulator sub-system results in a final system and method that (1) yields advantages and benefits that are more than what would be expected, and (2) yields advantages and benefits that would not be gained by simply making any other seemingly equivalent combination. Advantages and benefits realized by the final system and method include faster surgery times, decreased risk of infection during surgery, more efficient and effective use of surgery resources and personnel, more accurate and precise application of surgical tools, and decreased need for a specialized, cumbersome set-up for use on the combined final system to make it operable.

In fact, there are countless examples of prior art patient positioning sub-systems that, if combined with prior art robotic surgical manipulator sub-system(s), would not yield the synergistic advantages and benefits as described in the present disclosure.

As such, prior art patient positioning devices would be representative of components that, if combined with a prior art robotic surgical manipulator sub-system, would not yield the synergistic advantages and benefits as described in the present disclosure. Combinations with most if not all of the prior art would at best be a sum of the components, if not less than the sum of the components. In stark contrast to this, the present solution realizes the synergistic combination of an autonomous patient positioning sub-system, with a robotic surgical manipulator sub-system, and suffers few to no complications.

For example, and related to complications, fixed/static prior art devices are those that are positioned, secured, or mounted on an operating table prior to the start of the surgical procedure. Once the procedure begins, such devices cannot be easily moved, adjusted, or re-positioned. Thus, if a surgical procedure requires that the patient be re-positioned during different parts of the procedure, the pior art currently teaches that surgery must be temporarily halted while the patient positioning device is moved or hand-adjusted, typically through the use of thumbscrews, levers, sliding bars, and the like.

Further, mechanically, electrically, or hydraulically-driven devices have also been suggested, which teach an apparatus for holding, maneuvering, and maintaining a body part of a patient during surgery. One embodiment of the device physically straps the upper leg and foot of a patient to supports that are movable using motor driven gears that provide lateral, tilting, and swinging movement. However, such a device is mechanically complex and requires sterilization of portions of the device that are located in the sterile operating field. Further, once the patient is strapped into the device, manual positioning of the leg is not possible. The present solution solves these problems.

Accordingly, the need exists in the art for an automated patient positioning device and method that is simple in construction, easy to install and position, and that can be used outside the sterile operating field, in conjunction with a robotic surgical manipulator sub-system.

Anthropometrics

It is envisioned that weight may be measured to the nearest 0.1 kg (with the subject's shoes, socks, and bulky clothing removed), with a single pair of electronic scales that will calibrate the weight. Height may be measured to the nearest 0.1 cm (with shoes and socks removed) using a stadiometer. Body mass index (BMI) may be calculated as weight (kg)/height (m$^2$).

Computerized Tomography (CT Scan)

A computerized tomography (CT) scan combines a series of X-ray images taken from different angles and uses computer processing to create cross-sectional images of the bones to provide more detailed information about the structure of the bones. It is envisioned that a CT scan may be used to visualize the whole joint of both the healthy knee or hip joint and the diseased knee or hip joint to allow for a customized fit, for example. Further, prior to the start of a procedure, pre-operative images of the location of the site on the patient at which the procedures are performed are generated. These images may be based on MRI scans, radiological scans or computed tomography (CT) scans of the surgical site. These images are mapped to the bone coordinate system, for example, using known methods.

Pre-Surgery Preparation—

Before treating a patient, certain preparations are necessary such as draping the patient and preparing the surgical site for treatment. For instance, in knee arthroplasty, surgical personnel may simply place and rest the leg/foot of interest upon the patient positioning sub-system, after having draped the patient and equipment. Other preparations include placing objects needed for surgery in the operating room. These objects can include leg holders, retractors, suction/irrigation tools, surgical personnel, and the like. During the surgery, these objects are to be avoided by the surgical instrument(s). To facilitate avoidance of these objects during the surgery, position information for one or more of these objects is determined either directly or indirectly. In some embodiments, one or more of the objects are dynamically tracked by the navigation sub-system during the surgery.

Hardware

Patient Positioning Sub-System—

It is envisioned, in one exemplary embodiment, that a patient positioning sub-system is provided and includes a support adapted to be positioned against a patient's heel; an electrically powered linear actuator as part of a drive mechanism, for moving the support along a generally linear path; a source of power for the drive mechanism; a bracket for mounting the drive mechanism to an operating table; and a remote device for actuating the drive mechanism.

More specifically, it is envisioned that the bracket is used to secure the drive mechanism to the support rail(s) of the surgery table, and that the drive mechanism is anchored to the bracket(s). Thumbscrews, clamps, or other attachment devices may be used. The bracket and attachments are designed so that the drive mechanism is readily moveable from one side of an operating table to an opposite side or end, depending upon the particular surgical procedure to be performed, or the demands of the virtual boundary. It also is envisioned that the actuator includes a motor, worm gearing, and a lead screw, and a thrust tube. Power to the motor causes rotation of the worm screw drive resulting in the thrust tube either extending or retracting. The remote device for actuating the drive mechanism controls power to the motor and is communicatively coupled to other components/sub-systems, such as a navigation sub-system and/or other processing unit. The linear actuator may be a commercially available device such as linear drives from Magnetic Corporation of Olney, Ill., a subsidiary of SKF Linear Motion. Further, the source of power for the drive mechanism is provided through an electrical plug.

It is envisioned, in one exemplary embodiment, that the support of the patient positioning sub-system is padded and cylindrical in shape, to provide additional comfort for a patient's heel/foot. The movable support is positioned under the patient's foot proximate or on the heel. Movement of the support causes flexing of the patient's knee to an optimal position for a surgical procedure, and for adjusting of the virtual boundaries as needed.

In this light, a method of controlling the support of the patient positioning sub-system is also provided. A navigation system, whether incorporated into the patient positioning sub-system and/or whether established as its own as an independent component in the system, cooperates with the patient positioning sub-system to position the support with respect to a boundary between tissue of the patient, to which the surgical instrument should be applied, and tissue of the patient to which the energy applicator should not be applied. The patient positioning sub-system and/or the movable support may then be actuated (with the motors and points of movement and/or overlap, positioned outside of the sterile operating field, below the sterile drape, for example), not interfering with a patient's, surgeon's, and/or other surgical assistant's movement.

In a preferred form, the support includes an extension, preferably angled, and the drive mechanism is coupled to the extension. The extension includes means for adjusting the height of the support. The means include a plurality of generally spaced openings on the extension and a pin for releasably locking the extension in a predetermined position through such spaced openings. In one exemplary embodiment, the support also includes an angled extension that either fits into or becomes a sleeve, wherein the height of the support is vertically adjustable by aligning different holes in the sleeve with a complementary opening at the end of a thrust tube, for example, and securing the thrust tube and sleeve with a linchpin, for example.

It is envisioned, in one exemplary embodiment, that the autonomous patient positioning sub-system is communicatively coupled with a navigation sub-system and therefore, directly or indirectly, to a surgical manipulator. The navigation sub-system is configured to cooperate with the patient positioning sub-system to position the support with respect to virtual boundaries that currently exist, and/or are calculated/expected to exist, as the surgery progresses.

The navigation sub-system is configured to track movement of various objects in the operating room. Such objects include, for example, surgical instrument(s), the femur of the patient, and the tibia of the patient, the retractor(s), the knee joint stabilizer(s), the patient positioning sub-system, or components and tissues related thereto. The navigation system also tracks these objects for purposes of operating the scheduled surgery routine, displaying their relative positions and orientations to the surgeon, for purposes of controlling or constraining movement of the surgical instrument, and/or the patient positioning sub-system, relative to virtual cutting boundaries, associated with the femur and tibia.

Navigation Sub-System—

It is envisioned, in one exemplary embodiment, that the navigation sub-system comprises a localizer, for example, an optical localizer comprising a sensing device, for example, an optical sensor. If an optical localizer, the camera unit may be mounted on an adjustable arm to position the optical sensors with the necessary field of view/exposure, ideally, free from obstruction. Position and orientation signals and/or data are transmitted to the navigation computer for purposes of tracking objects. Other types of localizers are envisioned.

More specifically, in one exemplary embodiment, the navigation sub-system is a personal computer or laptop computer. Navigation computer has a display, central processing unit (CPU) and/or other processors, memory, and storage. The navigation computer is loaded with software. The software converts the signals received from the localizer into data representative of the position and orientation of the objects being tracked. One of ordinary skill in the art would understand how to code the necessary software in view of this disclosure.

Further, the navigation sub-system includes a navigation processor and a boundary generator module operable on the navigation processor. The boundary generator module is configured to generate the boundary based on a plurality of inputs. In certain exemplary embodiments, the system comprises a support portion tracking device to track movement of the support and the necessary software, for example, a localization engine configured to receive data from the localizer. The system also comprises a first boundary tracking device to track movement of a first of the plurality of virtual boundaries wherein the first virtual boundary is associated with the anatomy to be treated. The system further comprises a second boundary tracking device to track movements of a second of the plurality of virtual boundaries wherein the second virtual boundary is associated with an object to be avoided by the instrument, etc.

Further, prior to the start of any surgical procedure, relevant data is loaded into the navigation processor. Based on the position and orientation of the tracking data, the navigation processor determines the position of the working end of the surgical instrument and the orientation of the surgical instrument relative to the tissue against which the working end is to be applied. In some embodiments, the navigation processor forwards the data or related data to a manipulator controller. The manipulator controller can then use the data to control a robotic manipulator. Further, in some embodiments of the present solution, the navigation processor forwards the data or related data to a controller sub-system. The controller sub-system can then use the data to control a motorized patient positioning sub-system.

Controller Sub-System—

It is envisioned, in one exemplary embodiment, that a controller sub-system, is configured to receive information from the navigation system and/or other components or sub-systems, to control a motorized support portion of a patient positioning sub-system. The controller also is configured to guide movement of the support portion of the patient positioning sub-system, for example, relative to each of the first and second virtual boundaries as the first and second virtual boundaries move relative to one another, or relative to other objects or tissue, during the surgery. In some exemplary embodiments, the controller is configured as a remote device (from the point of the view of the patient positioning sub-system) for actuating the drive mechanism of the patient positioning sub-system.

More specifically, in one exemplary embodiment, the controller sub-system is a personal computer or laptop computer. The controller sub-system has a display, central processing unit (CPU) and/or other processors, memory, and storage. The controller sub-system is loaded with software.

Further, the navigation system may leverage a plurality of dynamic virtual boundaries to guide movement of the patient positioning sub-system via the controller sub-system. The navigation system leverages the modeled virtual constraint boundaries, to actuate, via the controller sub-system, motors that drive movement of the support of the patient positioning sub-system. The models may be displayed on the display of the remote, controller sub-system to show how movement of the patient positioning sub-system affects locations of the surgery objects and the virtual boundaries. Further, the controller sub-system may be configured to communicate with the manipulator controller, for example, to guide the manipulator relative to these virtual constraint boundaries, and relative to the movement of the patient positioning sub-system.

In this way, the device of the present solution provides convenience for the surgeon by permitting remote and automous "smart" operation of the drive mechanism of the patient positioning sub-system. The present solution also provides a method for positioning a patient during a surgical procedure comprising positioning a patient on an operating table; positioning a movable support against a predetermined portion of a patient's body outside of the sterile operating field; causing the support to move by automatically actuating a drive mechanism to provide linear movement of the support to cause the patient to move to an optimal position for a surgical procedure in uninterrupted fashion.

Robotic Surgical Manipulator Device—

It is envisioned, that the instrument or tool of the robotic surgical manipulator device may be configured as, but not limited to: burs; drill bits; saw blades; ultrasonic vibrating tips; electrode tips; RF electrodes; cauterizing and ablation tips; and light emitting tips.

Software—

It is envisioned, in one exemplary embodiment, that software modules are run on the navigation processor, or the controller sub-system, or any other component comprising a processor and memory. One of these modules is a boundary generator that generates a map that defines one or more boundaries between the tissue to which the instrument should be applied and the tissue to which the instrument should not be applied. An input into the boundary generator may include preoperative images of the site on which the procedure is to be performed, and/or the Computerized Tomography (CT Scan) information, and/or the anthropometrics information. If the manipulator/instrument is used to selectively remove tissue so the patient can be fitted with an implant, a second input into the boundary generator is a map of the shape of the implant, dimensions and size information, variance in manufacture, etc. Further, an input into the boundary generator is the surgeon's settings. These settings include the practitioner's settings indicating to which tissue the instrument should be applied. If the instrument is used to remove tissue, the settings identify the boundaries between the tissue to be removed and the tissue that remains after application of the instrument. If the manipulator is used to assist in the fitting of an orthopedic implant, these settings define where over the tissue the implant should be positioned. Other inputs are envisioned. Based on the input data and instructions, boundary generator generates a map that defines the instrument boundaries.

Another one of these exemplary modules is a tool path generator that may receive the same general input(s) as those applied to the boundary generator. Based on these inputs, the tool path generator generates a tool path. The tool path generator receives as inputs, for example, the image of the tissue, data defining the shape of the boundary, and the surgeon's setting regarding the location of the boundary. For an orthopedic surgical procedure, the boundary is typically the shape of the implant; the surgeon setting is often the position of the implant. Once a procedure begins, the tool path generator may also receive additional data. Based on this data, the tool path generator may revise the tool path. It should be appreciated that, based on this data, the tool path generator defines the tool or cutting path. It should also be appreciated that, based on this data, boundary constraints are generated for the tool or cutting path.

Another one of these exemplary modules is a localization engine that receives as inputs data, for example, sensor data and tracking data, regarding the surgical instruments, patient tissue, system components and sub-systems. Based on these signals, in one exemplary embodiment dealing with the patient positioning sub-system, the localization engine determines the position and pose of the bone(s), and the state of the patient positioning sub-system, and the orientation and positioning of the components thereof. Further, the localization engine forwards the signals representative of its work to a coordinate transformer, for example.

Another one of these exemplary modules is a coordinate transformer that references the data that defines the relationship between the preoperative data of the patient, tool, and system, etc. and the current state thereof. The coordinate transformer may also store the data indicating the relative nature of surgical object and tissue as compared to other surgical objects and tissue.

Another one of these exemplary modules is a removed material logger that contains a map of the volume of the tissue to which the instrument is to be applied. Often this is a map of a volume of tissue that is to be removed. Other data that goes into maintaining this map may come from the data describing the shape of the implant and the personal setting of the surgeon, and the data related to how changing the patient positioning device affects the position and pose of the bone(s). Other sources of data for defining this volume including mapping data obtained at the start of the procedure. Further, the logger may also collect data identifying the on-patient locations to which the instrument is to be applied, not to be applied, has already been applied, etc. This data may be based on the manipulator tracking the movement of the arms, the platform of the patient positioning system, etc. This data may be based on the commanded or measured pose data. Alternatively, this data may be generated based on the data describing the movement of the tool tracker. Further, the logger may transform the data regarding movement of the instrument and the tool tracker into data that defines where, relative to the bone, the instrument has moved, and possibly how the patient positioning sub-system contributed to this. The logger stores the data.

Another one of these exemplary modules is actually a set of modules that perform behavior control. Behavior control is the process of generating instructions that indicate the next commanded pose for the instrument. A second set of software modules perform motion control. One aspect of motion control is the control of the manipulator. The motion control process receives data defining the next commanded pose of the instrument from the behavior control process, for example. Based on this data, the motion control process determines the next position of the joint angles of manipulator, for example. A second aspect of motion control is the providing feedback to the behavior control modules based on the constraints of the manipulator. The motion control modules also monitor the state of the manipulator to detect if external forces/torques are being applied to or objects are in contact with the manipulator or instrument or any component of the system.

Certain embodiments disclosed will become more apparent from the drawings and following description.

FIG. 1 is an illustration of an exemplary embodiment of a new and useful system that positions a patient, via an autonomous patient positioning sub-system, and which operates in conjunction with a robotic surgical manipulator device. The system 1 positions a patient as needed for the surgery, via a patient positioning sub-system 10, wherein the positioning of the patient is an autonomous mode, coordinated with the application of the surgical instrument 160. The positioning of the patient is based at least in part on the demands and requirements and boundary-requirements, etc. of the manipulator 50, the surgical navigation system 210, the controller sub-system 36 of the patient positioning sub-system 10.

An exemplary manipulator 50 used to apply a surgical instrument 160 to a patient 600 is shown. The manipulator 50 comprises an end effector 110 to which the surgical instrument 160 is attached. The manipulator 50 positions the end effector 110 to position and orient the surgical instrument 160 so that the instrument performs the intended medical/surgical procedure on the patient 600. The manipulator 50 is used in conjunction with a surgical navigation system 210 and a controller sub-system 36, as well as various other components described herein.

The manipulator 50 includes a cart 52. The cart 52 includes a wheel-mounted frame. A shell 56 is disposed over the frame. The manipulator 50 includes lower and upper arms 68 and 70, respectively. Each arm 68 and 70 includes a four bar linkage. In certain exemplary embodiments, the manipulator 50 includes a number of interconnected links. These links may be connected together in series and/or parallel. These links may form two parallel four bar linkages with the necessary actuators and electrical motors, as is understood by a person having ordinary skill in the art. The instrument 160 is connected to the distal end of the links. Generally each pair of adjacent links is connected by a joint. The position of the links is set by actuators associated with the joints.

The surgical navigation system 210 monitors the position of the end effector 110 and the patient 600 and the patient positioning sub-system 10. The navigation sub-system 210 comprises a localizer 216 comprising optical sensor(s), and other sensors to successfully track objects and tissue during the surgery. The localizer 216 receives signals from, or transmits signals to, the trackers on objects and tissue for the surgical procedure. If the localizer 216 receives light signals from the trackers, the localizer is called a camera or optical localizer. The surgical navigation system 210 also includes a navigation processor 218. If the localizer 216 receives signals from the trackers, the localizer 216 outputs to the processor 218 signals based on the position and orientation of the trackers relative to the localizer. If the trackers receive signals from the localizer 216, the trackers output to the processor 218, based on the position and orientation of the trackers to the localizer, or via some other indirect localizing method.

Based on the received signals, the navigation processor 218 generates data indicating the relative positions and orientations of the trackers to the localizer 216. In some versions, the surgical navigation system 210 may include the trackers, sensor system, localizer, and/or computer systems.

Based on this monitoring, the surgical navigation system 210 determines the position of the surgical instrument 160 relative to the site on the patient to which the instrument is applied, and the position of the patient positioning sub-system 10. Further, a path of travel along which the instrument 160 should be applied to the patient tissue is generated. At least the basic version of this path may be generated prior to the start of the procedure. The surgical navigation system 210 calculates the forces and torques necessary to move the instrument along a predefined path of travel. Based on these forces and torques, the manipulator 50 moves the surgical instrument 160, via the end effector 110, along the predefined path of travel.

More specifically, prior to the start of the surgical procedure, additional data is loaded into the navigation processor 218. Based on the position and orientation of the trackers, or the data received from component sensors and processors, and the previously loaded data, the navigation processor 218 determines the position of the working end of the instrument 160 and the orientation of the end effector 110, and the position of the platform, etc. The navigation processor 218 forwards this data to the manipulator controller 124. Further, the controller sub-system 36 (see FIG. 2 and the related Disclosure for a more detailed description) forwards this data to the motor 26 of the patient positioning sub-system 10.

Next, the manipulator 50 responds to the forces and torque commanded by the surgical navigation system 210 on the instrument 160 to position the instrument 160. In response to these forces and torques, the manipulator 50 mechanically moves the instrument 160 in a manner that emulates the intended path. As the instrument 160 moves, the surgical manipulator 50 and surgical navigation system 210 cooperate to determine if the instrument 160 is within the target boundary. This boundary is within the patient 600 and beyond which the instrument 160 should not be applied. The manipulator 50 selectively limits the extent to which the instrument 160 moves. Further, the manipulator 50 constrains the end effector 110 from movement that would otherwise result in the application of the instrument 160 outside of the defined boundary, via updated monitoring and analysis of the real world surgical conditions.

Said another way, the virtual cutting boundaries are created to delineate sections available to the instrument 160 and section restricted to the instrument 160. The surgical navigation system 210, via the localizer 216, tracks movement of the end effector 110/instrument 160 with respect to the virtual cutting boundary to determine a position and/or orientation of the end effector 110/instrument 160 relative to the virtual cutting boundary. Further, as is discussed in greater detail herein, prior to the start of the procedure additional data was loaded into the navigation processor 218. Based on the position and orientation of the trackers (which may have been applied by the surgeon to patient 600 to define the surgical site), and the previously loaded data, and the virtual cutting boundaries, and the state of the patient positioning sub-system 10, etc., the navigation processor 218 forwards the data to the manipulator controller 124 and the controller sub-system 36 (see FIG. 2 and the related Disclosure for a more detailed description). The navigation processor 218 also generates image signals that indicate the relative position of the instrument 160 to the surgical site.

These image signals are applied to an interface 220, also part of the surgical navigation system 210 in this embodiment. The interface 220, based on these signals, generates images that allow a surgeon to view the relative position of the instrument 160 to the surgical site. The interface 220 includes a touch screen, or other input/output device that allows entry of commands, and is situated outside of the sterile field.

Further, the patient positioning sub-system 10 is configured for positioning the patient 600 on an operating table 12. The operating table 12 is segmented and includes a head and upper body support section 14, a trunk support section 16, and a leg support section 18. The operating table 12 also includes a pair of stand-off rails 20 substantially running the length of the operating table 12.

The patient positioning sub-system 10 includes a support 22 that is adapted to be positioned beneath the patient's foot, specifically, up against the heel and/or arch of the foot of the patient 600. The patient positioning sub-system 10 also includes a drive mechanism 24 for moving the support 22 along a generally linear path towards the feet/bottom of the operating table 12 or towards the top/head of the operating table 12. The drive mechanism 24 is configured, at least in part, as an electrically powered linear actuator. The actuator includes a motor 26 with a worm gearing and a lead screw, and a thrust tube 28. Power to the motor 28 causes rotation of the worm-screw-drive resulting in the thrust tube 28 either extending or retracting.

The bracket 30 is used to secure the drive mechanism 24 to the support rail 20. Thumbscrews, clamps, or other attachment devices are used. The bracket 30 and attachments are designed so that the drive mechanism 24 is readily moveable from one side of an operating table 12 to an opposite side or end, depending upon the particular surgical procedure to be performed. Further, the drive mechanism 24 is driven by the electric motor 26. A source of power for the drive mechanism 24 is provided through electrical plug 32.

The support 22 is padded for the comfort of patient 600. In the embodiment shown, the support 22 is in the form of a cylinder. The support 22 includes an angled extension 38 that either fits into or becomes a sleeve 40. The sleeve 40 includes a plurality of spaced openings 42 that extend through the sleeve 40. In the embodiment shown, the height of the support 22 is vertically adjustable by aligning different holes 42 in the sleeve 40 with a complementary opening at the end of the thrust tube 28 and securing the thrust tube and sleeve with a linchpin 44.

In use, the patient 600 is positioned on operating table 12 and the patient positioning sub-system 10 is installed so that movable support 22 is properly positioned against the patient's foot, without need for straps or engagement, and the patient 600 is resting free on the movable support 22. As shown, the patient positioning sub-system 10 of the present solution is positioned and used outside of the sterile operating field and does not interfere with the surgeon's and/or surgical assistant's movements. This is in stark contrast to the prior art.

In particular, the movement of support 22 causes flexing of the knee of patient 600 to an optimal position for a surgical procedure, and for adjusting of the virtual boundaries, as needed. The patient positioning sub-system 10 is actuated at the movable support 22, with the motor 26 and the thrust tube 28, and other electronics and points of mechanical-overlap, such as the bracket 30, the electrical plug 32, the angled extension 38, the sleeve 40, the spaced openings 42, and the linchpin 44, and the controller sub-system 36, positioned outside of the sterile operating field, below the sterile drape 58.

In this light, a method of controlling the support 22 of the patient positioning sub-system 10 is provided. The surgical navigation system 210, despite being illustrated and enabled as its own independent component in the system 1, cooperates with the patient positioning sub-system 10 components to position the support 22 based at least in part on the virtual boundaries. The navigation processor 218 determines the relative location of the instrument 160 to a boundary, and via the controller sub-system 36 determines the relative location/positioning of the support 22 of the patient positioning sub-system 10 with the patient 600 in place (see FIG. 2 and the related Disclosure for a more detailed description).

In the event it appears that the navigation processor 218 demands, requires, or needs positioning of the instrument 160 beyond the boundary, the manipulator 50 does not allow this movement of the instrument 160. Instead, should the navigation processor 218 determine that the needed path/point for the instrument 160 would result in the instrument 160 triggering or exceeding a boundary, which the instrument 160 should not cross, the navigation processor 218 directly or indirectly (1) prevents the instrument 160 from movement beyond the boundary, and (2) adjusts the support 22 of the patient positioning sub-system 10 and/or any other component or sub-system of the patient positioning sub-system 10, such as the motor 26 and the thrust tube 28, to reposition the tissue to be treated, and (3) reassesses/determines the relative location of the instrument 160 to the new boundary condition, after adjustment of the patient positioning sub-system 10 at (2). The robotic surgical manipulator device 50 may then continue to attempt to move the instrument as demanded, required, or needed prior to (1).

Figure 2:
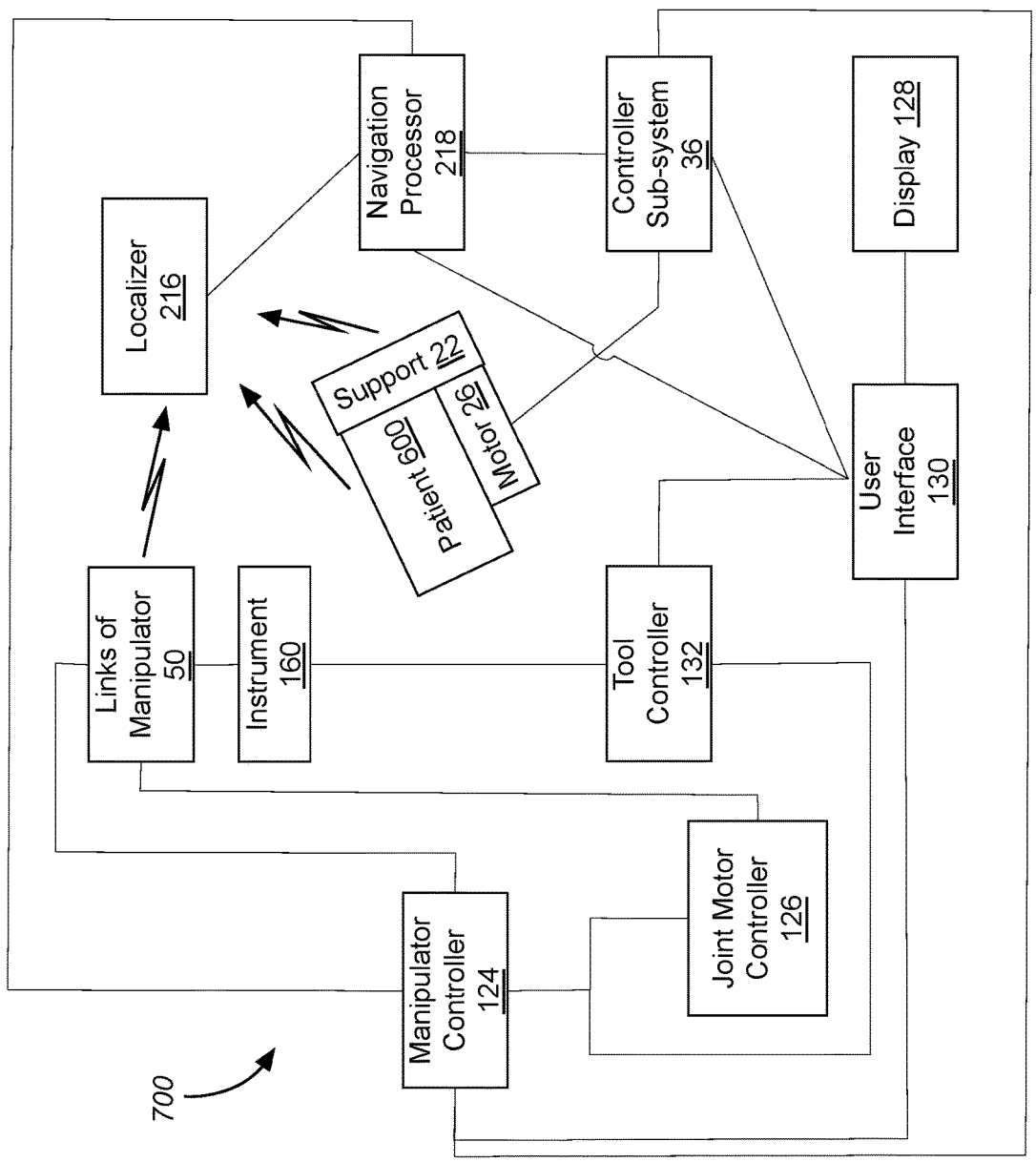
FIG. 2 is a block diagram of a number of modules that collectively cooperate to control actuation of the overall system of FIG. 1.

FIG. 2 is a functional block diagram of a number of modules that collectively cooperate to control actuation of the overall system 1 of FIG. 1. Mounted to cart 52 is a manipulator controller 124 and a joint motor controller(s) 126. The manipulator controller 124 is a high speed general purpose digital computer in this embodiment. The manipulator controller 124 determines the location to which the surgical instrument 160 should be moved based on data from force/torque sensors, encoders, the surgical navigation processor 218, as well as other information for the other portions of the system 1 as is described herein. Based on this determination, the manipulator controller 124 determines the extent to which each arm-forming link needs to be moved in order to reposition the surgical instrument 160 and/or guide the surgical instrument 160 along a desired path. The data regarding where the links are to be positioned are forwarded to the joint motor controllers 126.

Each joint motor controller 126 regulates the application of energization signals to a single one of the joint motors. The primary function of the joint motor controller 126 is to apply energization signals to the associated motor so that the motor drives the associated joint to an angle that approaches the commanded joint angle.

A touch screen display 128 or other user input/output unit is also mounted to cart 52. The display 128 is attached to a user interface 130 also attached to the cart. The user interface 130 controls the presentation of information on the display 128 and initially processes user-generated commands/inputs entered over the display 128.

The tool controller 132 supplies energization signals to the surgical instrument 160. The tool controller 132 typically includes: a power supply; power control circuit; a user interface; an application specific data processing unit (components not illustrated). The power supply converts the line voltage into power signals that can be applied to the surgical instrument 160. The power controller circuit selectively applies the power signals to the power generating unit integral with the instrument 160.

In some embodiments, the manipulator display 128 functions as the user interface and output display for the tool controller 132. The user interface 130 allows the practitioner to enter instructions regarding how she/he wants the instrument 160 to function as a back stop to the automation provided by the system 1. Commands to set and adjust the operational settings of the tool controller 132 and instrument 160 are forwarded from the user interface 130 to the tool controller 132.

The tool controller 132 receives the instructions entered over the user interface 130 and other data necessary to operate the instrument 160 as is described in detail herein. Based on this data, the tool controller 132 outputs energization signals that cause the instrument 160 to operate in the manner instructed by the navigation processor 218, and the manipulator controller 124, and the other components that contribute to automation of the system 1.

For example, the controller sub-system 36, is configured to receive information from the navigation processor 218 and/or other modules, and transmit communication signals to the tool controller 132, as needed, to control the motorized support portion 22 of the patient positioning sub-system 10, based at least in part on at least a first and second virtual boundaries ascertained by the navigation processor 218, as well as other information from the other portions of the system 1 as is described herein. The controller sub-system 36 also is configured to guide movement of the support 22, for example, relative to each of the first and second virtual boundaries as the first and second virtual boundaries are moved/commanded to be moved, relative to one another, or relative to other objects or tissue, during the surgery.

Like the tool controller 132, the controller sub-system 36 supplies energization signals to the motor 26. The controller sub-system 36 typically includes: a power supply; power control circuit; a user interface; a data processing unit. The power supply converts the line voltage into power signals that can be selectively applied to rotate the worm gearing and a lead screw in the motor 26, resulting in the thrust tube 28 either extending or retracting. The user interface 130 also allows the practitioner to enter instructions regarding how she/he wants the motor 26 to function, as a back stop to the automation provided by the system 1.

In some exemplary embodiments, the manipulator display 128 functions as the user interface and output display for the controller sub-system 36. Commands to set and adjust the operational settings of the controller sub-system 36 and motor 26, etc., are forwarded from the user interface 130 to the controller sub-system 36.

Figure 3:
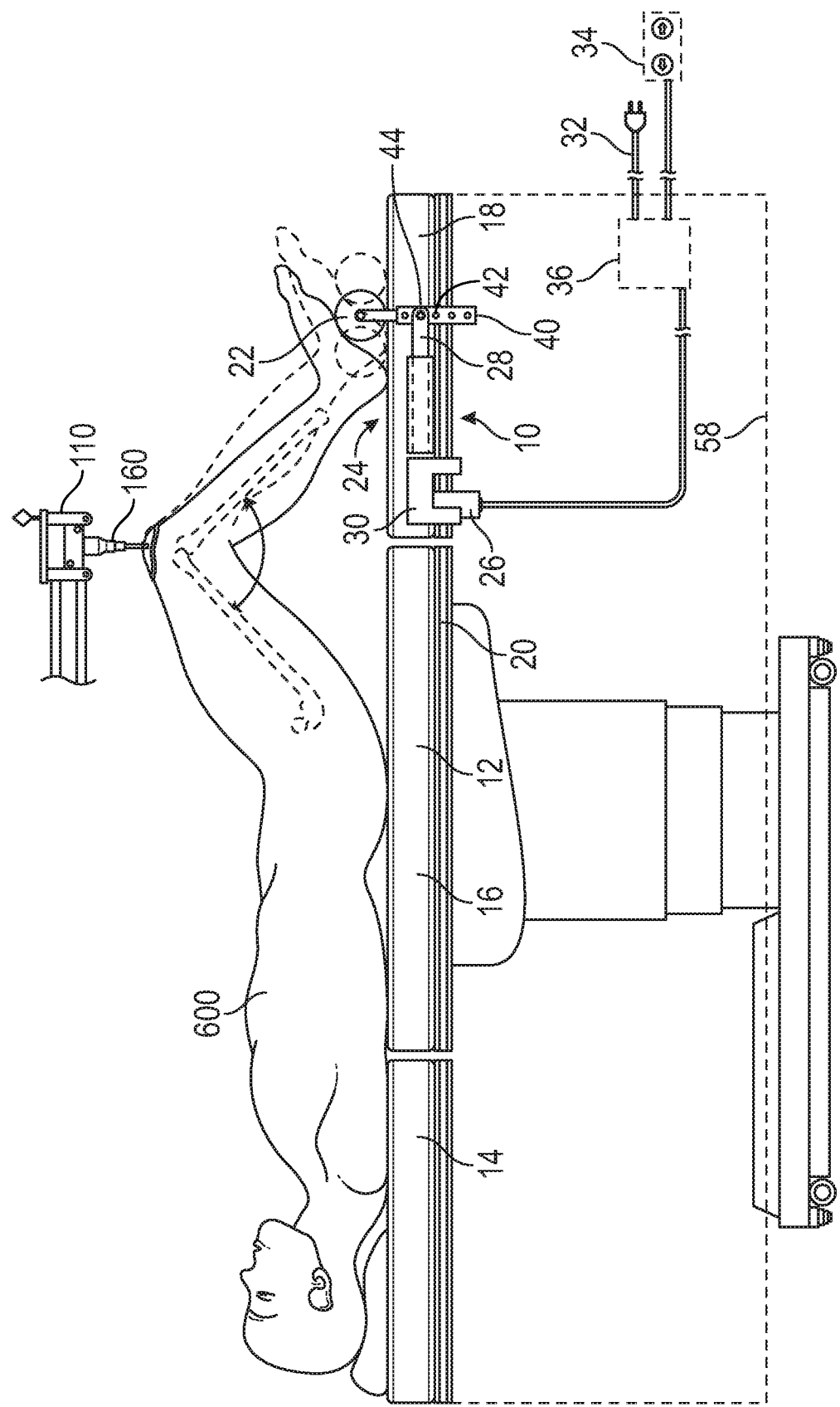
FIG. 3 is a magnified, side view of the exemplary system of FIG. 1.

FIG. 3 is a magnified, side view of the exemplary system of FIG. 1. As is described in greater detail herein, in some surgical procedures, it is necessary to move the limb of the patient 600 to a first position for initial work, and then to move that limb or body portion to second, third or more optimal positions as the surgery proceeds. In this way, the surgical boundaries may be modified or adjusted throughout the surgery. Although the system 1 automates the movement of the patient positioning sub-system 10, in conjunction with the automation of the manipulator 50 (partially shown), under some circumstances, the surgeon may need to remotely command the system 1.

For purposes of the patient positioning sub-system 10, the surgeon may use a foot-operated switch 34 to remotely actuate the drive mechanism of the motor 26. Again, as is described herein, all of this is outside the sterile surgical field beneath the drape 58. Depending on the motion desired, the surgeon may cause the thrust tube 28 to move as shown in FIG. 3 by pressing on the corresponding end of the switch 34. Activation of switch 34 causes the controller sub-system 36 to drive motor 26 in a desired direction.

Further, the controller sub-system 36 receives the instructions entered over the user interface 130, or foot-operated switch 34, and other data necessary to operate the motor 26, as is described in greater detail herein. Based on this data, the controller sub-system 36 outputs energization signals that cause the motor 26 to operate in the manner instructed by the controller sub-system 36, the navigation processor 218, and the manipulator controller 124, and the other components that contribute to automation of the system 1, as is described in greater detail herein.

In this way, the navigation processor 218 may leverage a plurality of dynamic virtual boundaries (not shown) and automated robotic surgery algorithms, and guide movement of the support 22 through commands from the controller sub-system 36. The navigation processor 218 leverages the modeled virtual constraint boundaries, to actuate, via the controller sub-system 36, movement of the support 22 of the patient positioning sub-system 10. The models used for automation may be displayed on a display 128 (not shown) to show how movement of the patient positioning sub-system 10 affects locations of the tracked objects (tracked objects previously placed along and around the surgical site by the surgeon). Further, the controller sub-system 36 communicates with the manipulator controller 124 (not shown) to help guide the links of the manipulator 50, and the corresponding movement of the surgical instrument 160, relative to these virtual constraint boundaries, and the movement of the patient positioning sub-system 10, etc.

Emphasis should be placed on the sterile drape 58 on the operating table 12. The drape 58 functions as a sterile barrier. Unlike prior art limb holders for arthroplasty, which are designed to be attached on top of the sterile drape 58, and which makes it difficult, if not impossible, to provide an optimal sterile barrier/easy-cleanup system, the patient positioning sub-system 10 is positioned directly on the operating table 12. The patient positioning sub-system 10 is installed such that the movable support 22 is properly positioned.

In this way, the entirety of the patient positioning sub-system 10 and the movable support 22, as well as the other structural and mechanical features of the system 1, other than the manipulator 50, are positioned, used, and/or actuated outside of the sterile operating field (e.g, below the sterile drape 58 with the patient's 600 leg exposed outside the sterile drape 58, the leg resting on top of the sterile drape 58, which is itself resting on top of the support 22). As the support 22 is cylindrical and configured to roll or skid on top of the operating table 12, as it is moved by the motor 26, the support 22 will not rip the sterile drape 58 even if the surgeon or the surgery personnel need to pull the sterile drape 58 in order to adjust the slack, etc. This maintains the integrity of the sterile operating field and positions any complex mechanical points of overlap, or pivot, or actuation, away from possible contamination, which would require difficult, costly, and complex sterilization and clean-up protocols.

Further, emphasis should be placed on the composition and positioning of the drive mechanism 24 of the system 1. The drive mechanism 24 is similarly and/or tangentially composed to the actuation mechanisms of the manipulator 50. This is of importance because the patient positioning sub-system 10 is easily implemented and incorporated into the autonomous surgical system, and into the software and hardware requirements, without necessitating extreme and/or complex changes.

As such, the system 1 provides convenience for the surgeon by permitting remote and automous "smart" operation of the drive mechanism of the patient positioning sub-system 10. The system 1 also provides a method for positioning a patient 600.

Referring now to FIG. 4, the FIGS. are a flow chart of an exemplary embodiment of a method of using the system of FIGS. 1-3. One of ordinary skill in the art understands that the exemplary method 1000 may be performed by various means that do not limit the scope of the present disclosure. The flowchart of the method 1000 is presented from the perspective of controlling the surgical manipulator 50 based on implant parameters, and on the position of the patient positioning sub-system 10. The manipulator 50, the navigation system 210, and the patient positioning sub-system 10 are envisioned to be employed in a surgical procedure to repair a joint of the patient 600, such as a knee joint, hip joint, shoulder joint, and the like.

Figure 4A:
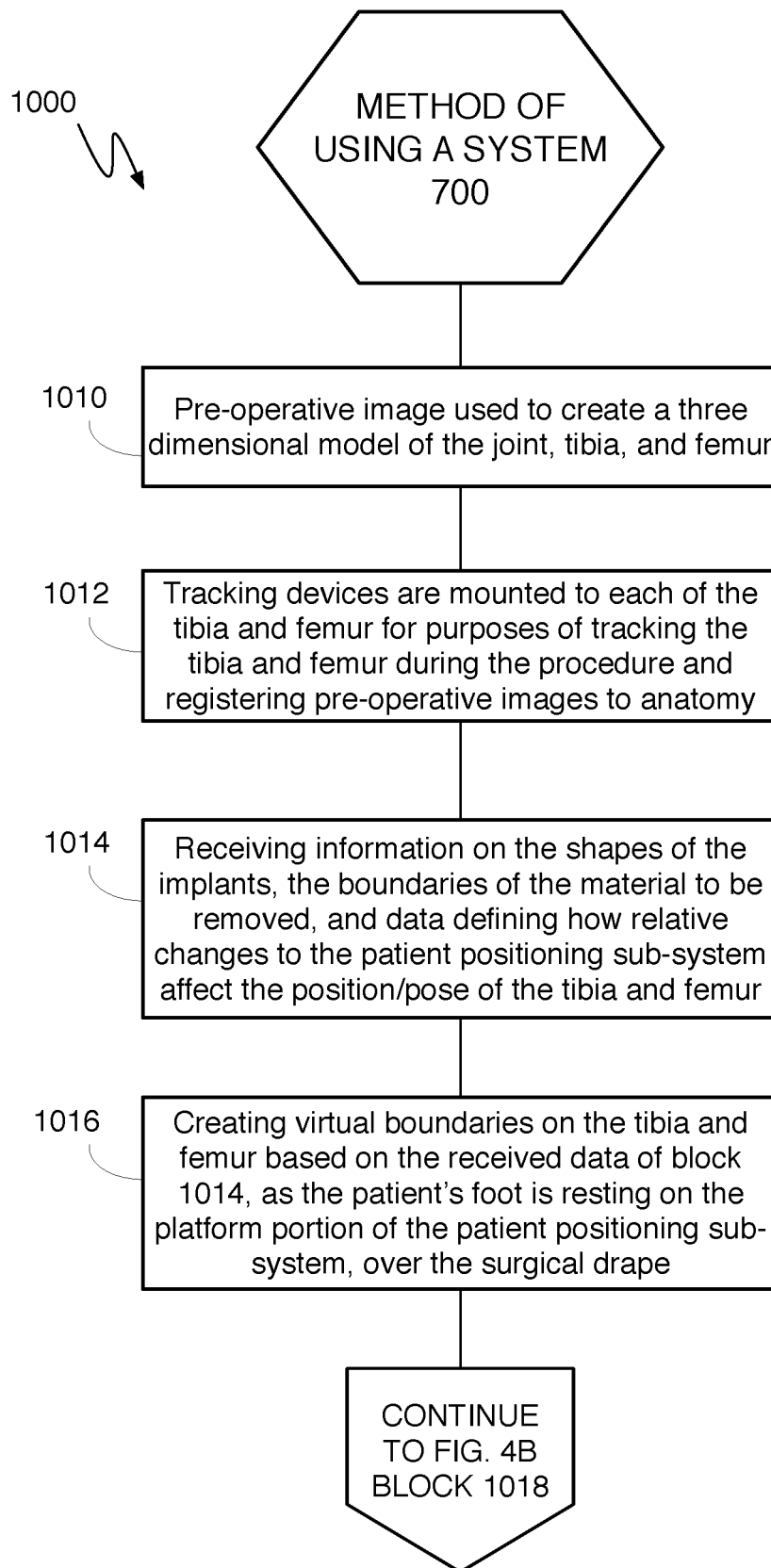
FIGS. 4A-4C are a flow chart of an exemplary embodiment of a method of using the system of FIGS. 1-3.

More specifically, at block 1010 of FIG. 4A, prior to the procedure, a pre-operative image, such as an MRI or CT scan is used to create a three dimensional model of the patient's joint. For instance, an MRI or CT scan is used to create a 3D model of the tibia and femur of the patient 600. At block 1012 of FIG. 4A, tracking devices with active or passive markers, are mounted to each of the tibia and femur of patient 600 using conventional methods, for purposes of tracking the tibia and femur during the procedure and for registering the pre-operative images to the anatomy.

At block 1014 of FIG. 4A, the navigation system 210 receives information on the shapes of the implants to be implanted on the femur and tibia of patient 600, the boundaries of the material intended to be removed from the patient's joint, and data defining how relative changes to the patient positioning sub-system 10 affect the position and pose of the femur and tibia of patient 600, etc. Measurements of the implants and the instrument 160 may be made by a coordinate measuring machine (CMM), laser measuring device, video measuring device, micrometer, profile projector, or other suitable devices.

At block 1016 of FIG. 4A, the navigation system 210 creates virtual boundaries on the femur and tibia of patient 600 based on the shapes of the implants and the current position of the joint, etc., as it is loosely resting on the platform portion 22 of the patient positioning sub-system 10, over the surgical drape 58. The three-dimensional shapes of the boundaries correlate to target volumes of material to be removed from the femur and/or tibia for the implants while the patient 600 is in that particular position and pose. The navigation system 210 includes the navigation processor 218 running boundary generator software operable to generate the boundary based on the plurality of inputs as described herein.

Notably, by tracking the positions and/or orientations of the instrument 160, the tibia, and the femur of the patient 600, and the current state of the patient positioning sub-system 10, during the procedure, the distal end or tip of the instrument 160 is maintained within the surgical boundaries. As the boundaries are tied to the anatomy of the patient 600, tracking movement of the anatomy also tracks movement of the boundaries since the anatomy of the patient 600 being treated may move during the surgical procedure.

Figure 4B:
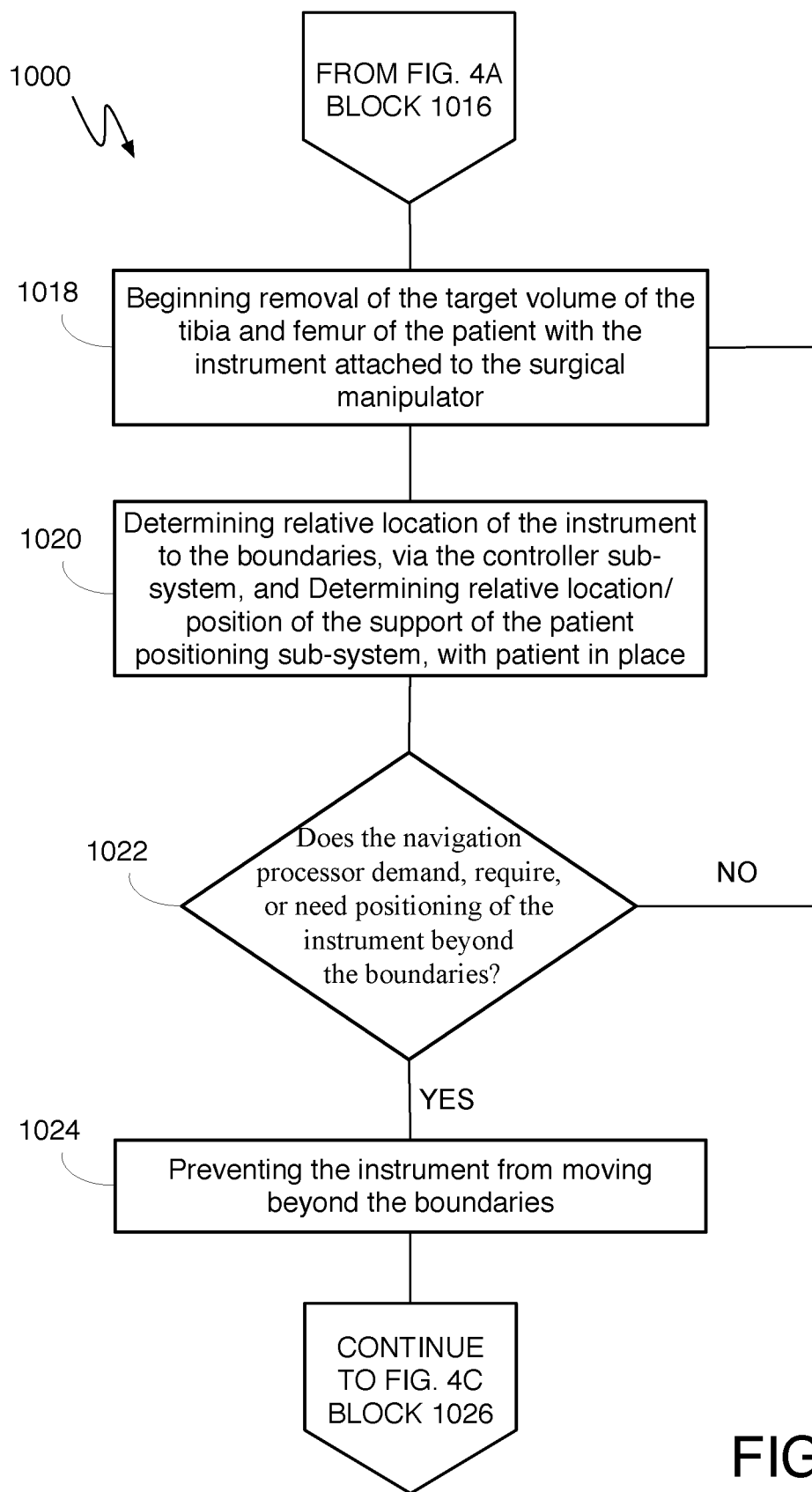

The method advances to block 1018 of FIG. 4B and includes the steps of beginning removal of the target volume of the femur and tibia of patient 600 with the instrument 160 attached to the surgical manipulator 50. At block 1020 of FIG. 4B, the navigation processor 218 determines the relative location of the instrument 160 to the boundary(ies), and via the controller sub-system 36, for example, determines the relative location/position of the support 22 of the patient positioning sub-system 10 with the patient 600 in place.

Notably, to perform this process, the controller 124 and the processor 218 and the controller sub-system 36, etc. collectively keep track of a number of different system 1 components and the patient 600.

At block 1022 of FIG. 4B, in the event it appears that the navigation processor 218 demands, requires, or needs positioning of the instrument 160 beyond the boundary, the navigation processor 218 does not allow this movement of the instrument 160. Instead, should the navigation processor 218 determine that the needed path/point for the instrument 160 would result in the instrument 160 triggering a boundary, which the instrument 160 should not cross, the navigation processor 218 directly or indirectly, at block 1024 of FIG. 4B, prevents the instrument 160 from moving beyond the boundary, and, at block 1026 of FIG. 4C, adjusts the support 22 of the patient positioning sub-system 10 via actuation of the motor 26 via the controller sub-system 36, for example, to reposition the joint being treated, and, at block 1028 of FIG. 4C, reassesses/determines the relative location of the instrument 160 to the new boundary condition after adjustment of the patient positioning sub-system 10 at block 1026. In this way, embodiments of the solution may very accurately, and precisely, position the patient's joint such that the boundaries of the surgical site are optimally defined for application of the surgical instrument 160.

As part of this re-positioning, the manipulator controller 124 does not move the instrument 160 outside of defined boundaries, but the controller sub-system 36 does position the platform 22 to adjust the defined boundaries, as needed and demanded by surgery. At block 1030 of FIG. 4C, in the event it again appears that the navigation processor 218 demands, requires, or needs positioning of the instrument 160 beyond the boundary, the navigation processor 218 does not allow this movement of the instrument 160. Instead, should the navigation processor 218 determine that the needed path/point for the instrument 160 would result in the instrument 160 triggering a boundary, which the instrument 160 should not cross, the method reverts back to block 1026. In the event that it does not appear that the navigation processor 218 demands, requires, or needs positioning of the instrument 160 beyond the boundary, the navigation processor 218 does allow the movement.

Figure 4C:
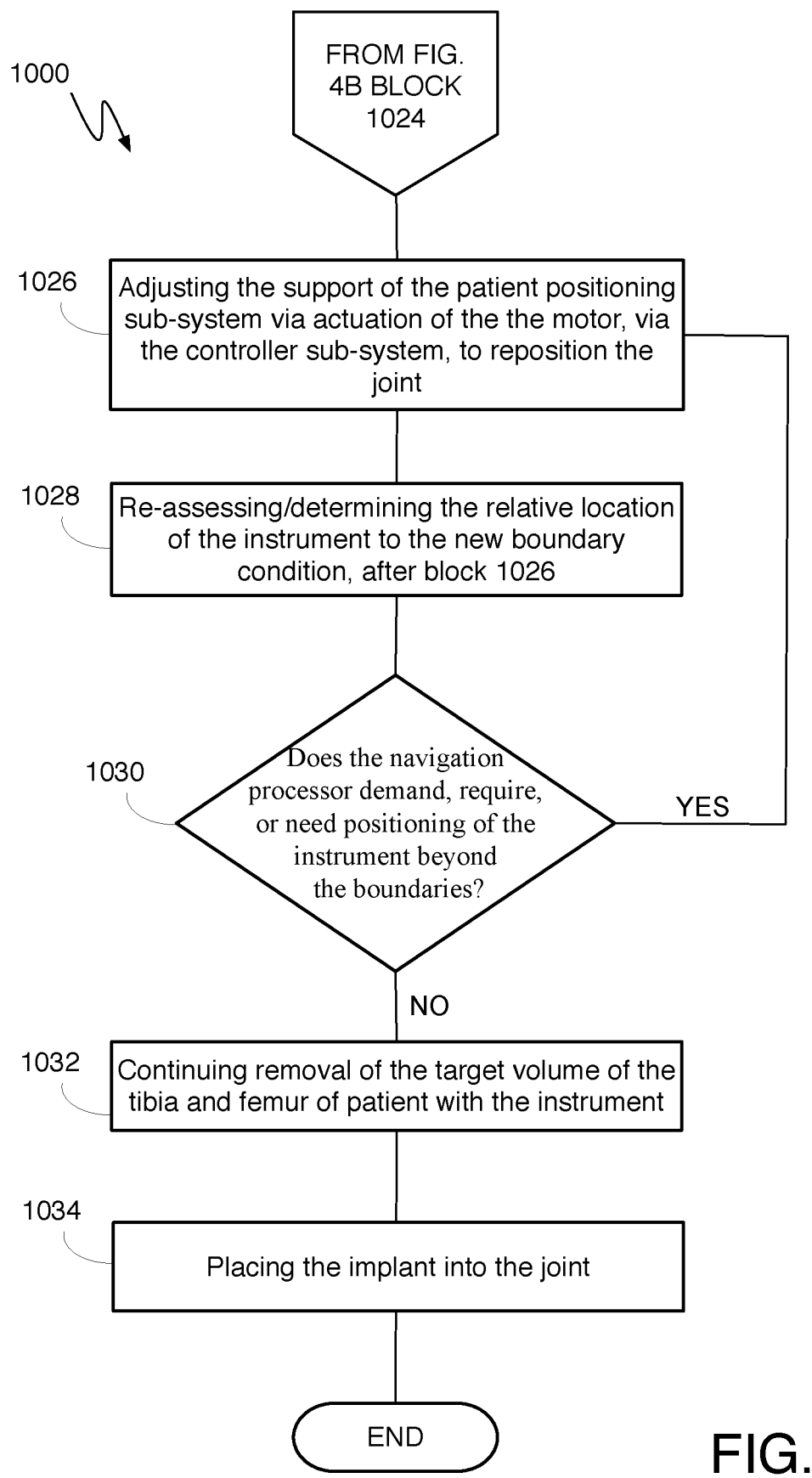

At block 1032 of FIG. 4C, the method advances and includes the steps of continuing removal of the target volume of the femur and tibia of patient 600 with the instrument 160. The method then advances to block 1034 of FIG. 4C and includes the steps of placing the actual implant into the joint. The method then ends.

In this way, the surgical navigation system 210 cooperates with the patient positioning sub-system 10 components to position the support 22 based at least in part on the virtual boundaries, based on the exemplary method of use as described herein. In other more detailed exemplary embodiments, the method may include the controller sub-system 36 receiving information from the navigation processor 218 and/or other modules, and transmitting communication signals to the tool controller 132, as needed, to control the motorized support portion 22 of the patient positioning sub-system 10, based at least in part on at least a first and second virtual boundaries, as well as other information from the other portions of the system 1, as is described herein. The controller sub-system 36 also may guide movement of the support 22, for example, relative to each of the first and second virtual boundaries as the first and second virtual boundaries are moved/commanded to be moved, relative to one another, or relative to other objects or tissue, during the surgery.

Certain steps in the exemplary method described herein naturally precede others for the solution to function as described. However, the solution is not limited to the order of the steps described if such order or sequence does not alter the functionality of the system and method of the present disclosure. That is, it is recognized that some steps may performed before, after, or parallel (substantially simultaneously with) other steps without departing from the scope and spirit of the solution. In some instances, certain steps may be omitted or not performed without departing from the solution. Further, words such as "thereafter", "then", "next", etc. are not intended to limit the order of the steps. These words are simply used to guide the reader through the description of the exemplary method.

Figure 5:
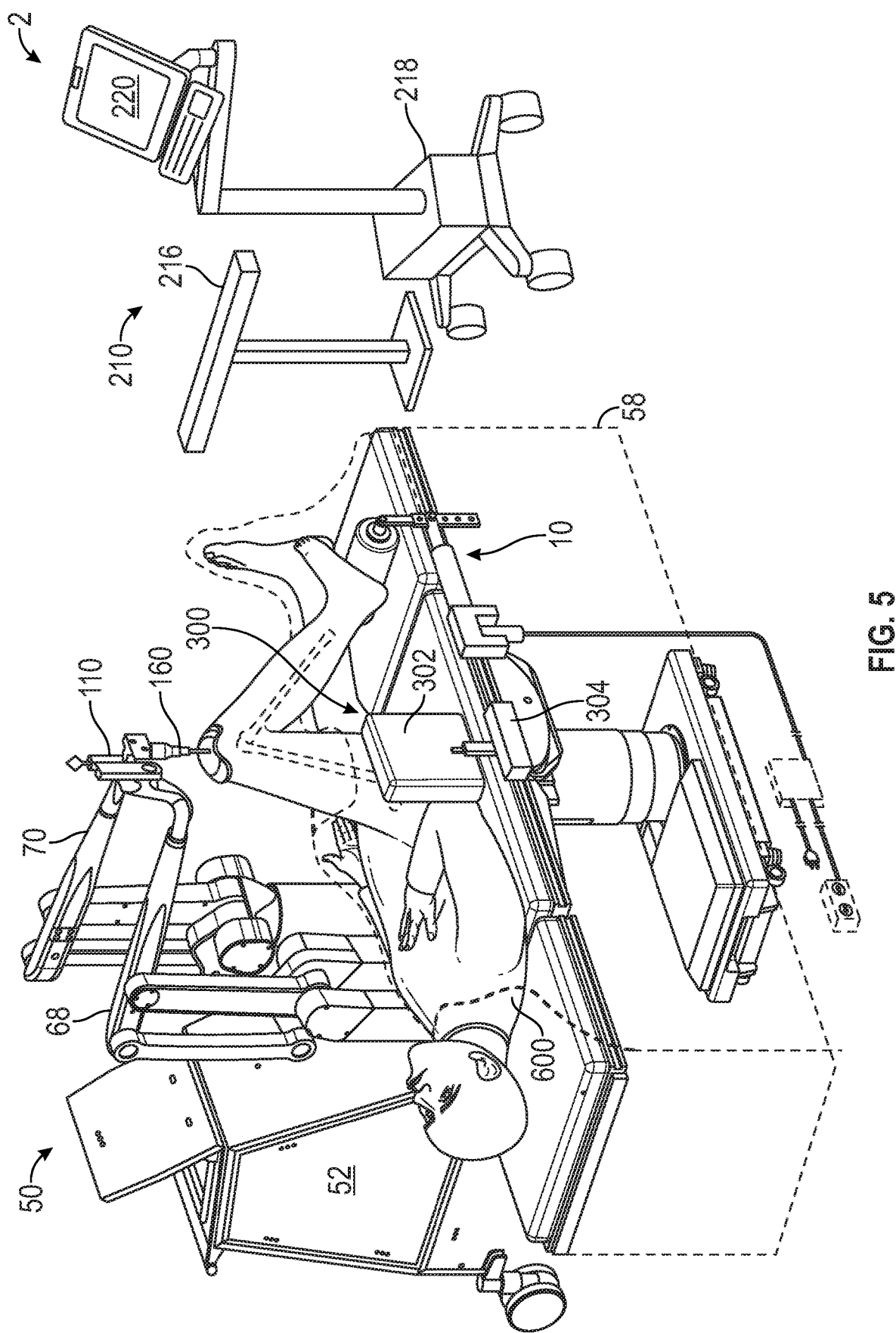
FIG. 5 is an illustration of a second exemplary embodiment of a new and useful system that positions a patient, via an autonomous patient positioning sub-system, and which operates in conjunction with a robotic surgical manipulator device, including an autonomous side pad.

FIG. 5 is an illustration of a second exemplary embodiment of a new and useful system that positions a patient, via an autonomous patient positioning sub-system, and which operates in conjunction with a robotic surgical manipulator device, which also includes an autonomous side pad 302. The system 2 is identical to the system 1 except for the following described differences.

The system 2 positions a patient as needed for the surgery, via a patient positioning sub-system 10 and a side pad sub-system 300, wherein the positioning of the patient is an autonomous mode, coordinated with the application of the surgical instrument 160. Again, the positioning of the patient is based at least in part on the demands and requirements and boundary-requirements, etc. of the manipulator 50, the surgical navigation system 210, and the controller sub-system 36 of the patient positioning sub-system 10.

The surgical navigation system 210 monitors the position of the end effector 110 and the patient 600 and the patient positioning sub-system 10 and the side pad sub-system 300. Based on this monitoring, the surgical navigation system 210 determines the position of the surgical instrument 160 relative to the site on the patient to which the instrument is applied, and the position of the patient positioning sub-system 10 and the position of the side pad sub-system 300. Further, a path of travel along which the instrument 160 should be applied to the patient tissue is generated.

More specifically, prior to the start of the surgical procedure, additional data is loaded into the navigation processor 218. Based on the position and orientation of the trackers, or the data received from component sensors and processors, and the previously loaded data, the navigation processor 218 determines the position of the working end of the instrument 160 and the orientation of the end effector 110, and the position of the platform 22, and the position of the side pad 302. The navigation processor 218 forwards this data to the manipulator controller 124. Further, the controller sub-system 36 forwards this data to the drive mechanism 24 of the patient positioning sub-system 10, and to the drive mechanism 304 of the side pad sub-system 300.

Next, the manipulator 50 responds to the forces and torque commanded by the surgical navigation system 210 on the instrument 160 to position the instrument 160. In response to these forces and torques, the manipulator 50 mechanically moves the instrument 160 in a manner that emulates the intended path. As the instrument 160 moves, the surgical manipulator 50 and surgical navigation system 210 cooperate to determine if the instrument 160 is within the target boundary. The manipulator 50 constrains the end effector 110 from movement that would otherwise result in the application of the instrument 160 outside of the defined boundary, via updated monitoring and analysis of the real world surgical conditions.

The navigation processor 218 forwards the data to the manipulator controller 124 and the controller sub-system 36, for controlling the patient positioning sub-system 10 and the side pad sub-system 300. The patient positioning sub-system 10 and the side pad sub-system 300 are configured for positioning the patient 600 on an operating table 12.

Similar to the patient positioning sub-system 10, the side pad sub-system 300 includes a side support/side pad 302 that is adapted to be positioned against the side of the patient 600, specifically, against the thigh of the patient 600 on the side to be operated on. The side pad sub-system 300 also includes a side pad drive mechanism 304 for laterally moving the side support 302 relative to the table 12 to adjust the lateral position of the patient's 600 leg. The drive mechanism 304 is configured, at least in part, as an electrically powered linear actuator with a shorter stroke length than the drive mechanism 24. As such, via a bracket like bracket 30, the drive mechanism 304 may be secured beneath the operating table 12 so as to leverage the shorter stroke length, while still positioning the drive mechanism 304 below the sterile surgical field/drape 58. Further, the side support 302 is padded for the comfort of patient 600. In the embodiment shown, the side support 302 is in the form of a planar padding.

In use, the patient 600 is positioned on operating table 12 and the patient positioning sub-system 10 and the side support 302 are installed so that movable support 22 is properly positioned against the patient's foot, and so that the movable side support 302 is properly positioned against the patient's outer thigh, without need for straps or engagement, and the patient 600 is resting free on the movable support 22, and naturally falling outwards toward the side pad 302 (due to patient's 600 unconscious state).

In particular, the movement of support 22 causes flexing of the knee of patient 600 to an optimal position for a surgical procedure, and for adjusting of the virtual boundaries, as needed. Similarly, the movement of side support 302 causes a lateral movement inward or outward of the knee of patient 600 to an optimal position for the surgical procedure, and for adjusting of the virtual boundaries, as needed. The patient positioning sub-system 10 is actuated at the drive mechanism 24 and the side support 302 is actuated at the drive mechanism 304.

In this light, a method of controlling the support 22 of the patient positioning sub-system 10 is provided, and a method of controlling the side support 302 of the side support sub-system 300. The surgical navigation system 210 cooperates with the patient positioning sub-system 10 components and the side support 302 components to position the support 22 and the side support 302 based at least in part on the virtual boundaries. The navigation processor 218 determines the relative location of the instrument 160 to a boundary, and via the controller sub-system 36 determines the relative location/positioning of the support 22 and the side support 302 with the patient 600 in place.

In the event it appears that the navigation processor 218 demands, requires, or needs positioning of the instrument 160 beyond the boundary, the manipulator 50 does not allow this movement of the instrument 160. Instead, should the navigation processor 218 determine that the needed path/point for the instrument 160 would result in the instrument 160 triggering a boundary, which the instrument 160 should not cross, the navigation processor 218 directly or indirectly (1) prevents the instrument 160 from movement beyond the boundary, and (2) adjusts the support 22 and/or the side support 302, and/or any other component or sub-system to reposition the tissue to be treated, and (3) re-assesses/determines the relative location of the instrument 160 to the new boundary condition, after adjustment of the patient positioning sub-system 10 and/or the side support sub-system 300 at (2). The robotic surgical manipulator device may then continue to attempt to move the instrument as demanded, required, or needed prior to (1).

Systems, devices and methods for a patient positioning system used to position body parts, such as a knee, during a medical or surgical procedure have been described using detailed descriptions of embodiments thereof that are provided by way of example and are not intended to limit the scope of the disclosure. The described embodiments comprise different features, not all of which are required in all embodiments of a magnetic prosthetic according to the solution. Some embodiments of the solution utilize only some of the features or possible combinations of the features. Variations of embodiments of the solution that are described and embodiments of the solution comprising different combinations of features noted in the described embodiments will occur to persons of the art.

It will be appreciated by persons skilled in the art that systems, devices and methods for a patient positioning system used to position body parts, such as a knee, during a medical or surgical procedure, according to the solution, are not limited by what has been particularly shown and described herein above. Rather, the scope of systems, devices and methods of a patient positioning system used to position body parts, such as a knee, during a medical or surgical procedure, according to the solution, is defined by the claims that follow.

System 1
System 2
Patient Positioning Sub-system 10
Operating table 12
Head and Upper Body Support Section 14
Trunk Support Section 16
Leg Support Section 18
Rails 20
Support 22
Drive Mechanism 24
Motor 26
The Thrust Tube 28
The Bracket 30
Electrical Plug 32
Foot-Operated Switch 34
Controller Sub-System 36
Angled Extension 38
Sleeve 40
Spaced Openings 42
Linchpin 44
Manipulator 50
Cart 52
Shell 56
Drape 58
Lower Arms 68
Upper Arms 70
End Effector 110
Manipulator Controller 124
Joint Motor Controllers 126
Display 128
User Interface 130
Tool Controller 132
Surgical Instrument 160
Surgical Navigation System 210

Localizer 216
Navigation Processor 218
Interface 220
Side Pad Sub-System 300
Side Pad 302
Side Pad Drive Mechanism 304
Patient 600
Method 1000

What is claimed is:

1. An apparatus for positioning a patient during a surgical procedure comprising:
  a cylindrical, padded support adapted to be positioned against the foot of a patient's body, the support comprising an extension, and the extension comprising means for adjusting the height of the support, the support also comprising an electrical drive mechanism with linear actuator for moving the support along a generally linear path, and a bracket for mounting the drive mechanism to the side of an operating table; and
  a remote device for actuating the drive mechanism, the remote device configured at least in part as a controller for the support, the controller communicatively coupled to a surgical navigation system, the surgical navigation system configured to cooperate with the controller to position the support with respect to a change demanded to a boundary, the boundary defining tissue of the patient to which an automated surgical instrument should be applied and tissue of the patient to which the surgical instrument should not be applied;
  wherein the remote device and the surgical navigation system are configured to be situated outside a sterile surgical field for the surgical procedure.

2. The apparatus for positioning a patient of claim 1, wherein the extension is angled.

3. The apparatus for positioning a patient of claim 1, wherein the drive mechanism is coupled to the extension.

4. The apparatus for positioning a patient of claim 3, wherein the extension defines a plurality of generally spaced openings.

5. The apparatus for positioning a patient of claim 4, further comprising a pin for releasably locking the extension in a predetermined position via the generally spaced openings.

6. The apparatus for positioning a patient of claim 1, further comprising a foot-operated switch for the remote device, as an emergency override to the surgical navigation system, the foot-operated switch configured to be communicatively coupled to the remote device, and situated outside the sterile surgical field and beneath the operating table.

7. The apparatus for positioning a patient of claim 1, wherein the surgical navigation system comprises a surgical tracker, a navigation processor, and a boundary generator module running on the navigation processor, and wherein the controller comprises a processor and a platform control module running on the remote device processor.

8. An apparatus for positioning a patient during a surgical procedure comprising:
  a cylindrical, padded support adapted to be positioned against the foot of a patient's body, the support comprising an extension, and the extension comprising means for adjusting the height of the support, the support also comprising an electrical drive mechanism with linear actuator for moving the support along a generally linear path, and a bracket for mounting the drive mechanism to the side of an operating table;
  a remote device for actuating the drive mechanism, the remote device configured at least in part as a controller for the support, the controller communicatively coupled to a surgical navigation system; and
  a side pad adapted to be positioned against the thigh of the patient's body, on the same side as the foot of the patient's body, the side pad comprising an extension to support the side pad, the side pad also comprising an electrical drive mechanism with linear actuator for laterally moving the side pad relative to the side of the operating table, and a bracket for mounting the drive mechanism to the side of an operating table, the remote device also configured for actuating the drive mechanism of the side pad, the surgical navigation system configured to cooperate with the controller to position the support and the side pad with respect to a change demanded to a boundary, the boundary defining tissue of the patient to which an automated surgical instrument should be applied and tissue of the patient to which the surgical instrument should not be applied;
  wherein the remote device and the surgical navigation system are configured to be situated outside a sterile surgical field for the surgical procedure.

9. The apparatus for positioning a patient of claim 8, wherein the extension for the support is angled.

10. The apparatus for positioning a patient of claim 8, wherein the drive mechanism for the support is coupled to the extension for the support.

11. The apparatus for positioning a patient of claim 10, wherein the extension for the support defines a plurality of generally spaced openings.

12. The apparatus for positioning a patient of claim 11, further comprising a pin for releasably locking the extension of the support in a predetermined position via the generally spaced openings.

13. The apparatus for positioning a patient of claim 8, further comprising a foot-operated switch for the remote device, as an emergency override to the surgical navigation system, the foot-operated switch configured to be communicatively coupled to the remote device, and situated outside the sterile surgical field and beneath the operating table.

14. The apparatus for positioning a patient of claim 8, wherein the surgical navigation system comprises a surgical tracker, a navigation processor, and a boundary generator module running on the navigation processor, and wherein the controller comprises a processor and a platform control module and a side pad control module running on the remote device processor.

* * * * *